(12) United States Patent
Zupancic

(10) Patent No.: US 7,884,212 B2
(45) Date of Patent: Feb. 8, 2011

(54) PROCESS FOR THE PREPARATION OF CANDESARTAN CILEXETIL

(76) Inventor: Silvo Zupancic, Zupnca 4b 8000, Novo mesto (SI)

( * ) Notice: Subject to any disclaimer, the term of this patent is extended or adjusted under 35 U.S.C. 154(b) by 95 days.

(21) Appl. No.: 12/089,444

(22) PCT Filed: Sep. 29, 2006

(86) PCT No.: PCT/EP2006/009489

§ 371 (c)(1),
(2), (4) Date: Sep. 8, 2008

(87) PCT Pub. No.: WO2007/042161

PCT Pub. Date: Apr. 19, 2007

(65) Prior Publication Data

US 2009/0318706 A1    Dec. 24, 2009

(30) Foreign Application Priority Data

Oct. 7, 2005  (SI) ................. 200500283
Mar. 3, 2006  (SI) ................. 200600041

(51) Int. Cl.
  *C07D 233/00*  (2006.01)
  *C07D 249/08*  (2006.01)
(52) U.S. Cl. .................... 548/250; 548/300.1
(58) Field of Classification Search ........... 548/250, 548/300.1

See application file for complete search history.

(56) References Cited

U.S. PATENT DOCUMENTS 5,578,733 A * 11/1996 Shida et al. ............. 548/253

FOREIGN PATENT DOCUMENTS

| EP | 0 459 136 A1 | 12/1991 |
| EP | 0 668 272 A2 | 8/1995 |
| EP | 0 720 982 A1 | 10/1996 |
| WO | 2005/037821 A2 | 4/2005 |
| WO | 2005/051928 A1 | 6/2005 |
| WO | 2005/021535 A2 | 10/2005 |
| WO | WO A 2007/074399 | 7/2007 |

OTHER PUBLICATIONS

Lu R J et al: "Detritylation with ytterbium triflate" Tetrahedron Letters, Elsevier, Amsterdam, NL, vol. 41, No. 16, Apr. 2000, pp. 2817-2819, XP004195678 ISSN: 0040-4039, p. 2817, paragraphs 1,4.
Römpp Lexikon: Lewis Säure [Online] 2006, Georg Thieme Verlag, XP002407601 Retrieved from Internet: URL: http://roempp.com> [retrieved on Nov. 15, 2006].
U.S. Appl. No. 60/687,305, Nuria Soldevilla Madrid.
U.S. Appl. No. 11/921,677, filed Jun. 6, 2006, Nuria Soldevilla Madrid.

* cited by examiner

*Primary Examiner*—Susannah Chung
(74) *Attorney, Agent, or Firm*—LaRiviere, Grubman & Payne, LLP

(57) ABSTRACT

The present invention provides an improved synthesis for the manufacture of candesartan and pharmaceutically acceptable salts and esters thereof as active ingredients of a medicament for the treatment of hypertension and related diseases and conditions which comprises the removal of the tetrazolyl protecting group in an organic solvent, and in the presence of a Lewis acid.

20 Claims, No Drawings

PROCESS FOR THE PREPARATION OF CANDESARTAN CILEXETIL

FIELD OF THE INVENTION

The present invention relates to an improved process for the manufacture of candesartan and pharmaceutically acceptable salts and esters thereof as active ingredients of a medicament for the treatment of hypertension and related diseases and conditions.

TECHNICAL PROBLEM

Candesartan cilexetil of formula (I) is chemically described as (+/−)-1-[[(cyclohexyloxy)carbonyl]oxy]ethyl-2-ethoxy-1-[[2'-(1H-tetrazol-5-yl)-1,1'-biphenyl-4-yl]methyl]-1H-benzimidazole-7-carboxylate. Because of its ability to inhibit the angiotensin-converting enzyme it is widely used for the treatment of hypertension and related diseases and conditions. As an angiotensin II receptor antagonist, candesartan cilexetil avoids the side-effects of calcium antagonists, and shows high stability and obvious curative effects. At the time being it is sold as the racemic mixture. It is produced according to published patents, e.g. EP 0 720 982 B1 and EP 0 459 136.

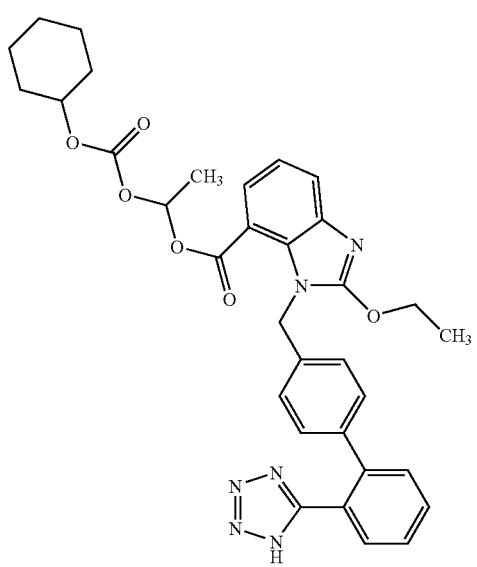

(I)

As is indicated herein below, it would be of great benefit to provide a more efficient and more economical technological process for providing candesartan cilexetil.

BACKGROUND OF THE INVENTION

EP 0 720 982 B1 discloses the preparation of candesartan cilexetil by the deprotection of the triphenylmethane (trityl) moiety, in methanol and in the presence of hydrochloric acid. The setbacks of this procedure are very low yields and the product needs to be purified by means of chromatography. EP 0 668 272 further teaches an improved deprotection procedure by using anhydrous hydrogen chloride in methanol. The yields are slightly improved in respect to EP 0 720 982 B1 but nonetheless the proportion of the decomposition products is still rather high. The drawbacks of the above mentioned methods are that they include the use of strongly corrosive acids and also the need to process the reaction mixture by complex extractions or chromatographic purification.

WO 2005/021535 discloses the preparation of candesartan cilexetil by the deprotection of the trityl moiety by solvolysis at reflux temperatures, in an anhydrous C1 to C5 alcohol under neutral or slightly basic conditions. The reported conversion to candesartan cilexetil is between 76% and 91% which is still not optimal in industrial production, and the reported reaction time is 24 hours, which is another setback from the industrial point of view. Further on, longer reaction times at reflux temperatures normally lead to higher levels of decomposition products.

WO 2005/037821 describes the deprotection of the tetrazolyl group from (+/−)-1-[[(cyclohexyloxy)carbonyl]oxy]ethyl-2-ethoxy-1-[[2'-(N-triphenylmethyltetrazol-5-yl)-1,1'-biphenyl-4-yl]methyl]-1H-benzimidazole-7-carboxylate (trityl candesartan cilexetil) by the use of methanesulfonic, p-toluene sulphonic, formic, and trifluoroacetic acid, or simply by refluxing trityl candesartan cilexetil in a mixture of toluene, methanol, and water. The drawbacks of these procedures are that the deprotection reaction is not completed properly and that the product is mostly isolated in form of a viscous oil due to impurities present.

WO 2005/051928 teaches processes for the production of tetrazolyl compounds including removing protective groups from an N-protected tetrazolyl compound, especially candesartan cilexetil, with organic acids. As low reaction temperatures, from 30° C. to 35° C. are applied, the yields are not higher that 60% and additional extractions and purifications with activated charcoal and by means of Celite are applied which is a clear sign for the presence of unwished side products and/or the presence of the starting material.

SUMMARY OF THE INVENTION

The present invention provides an improved synthesis for the manufacture of candesartan and pharmaceutically acceptable salts and esters thereof as active ingredients of a medicament for the treatment of hypertension and related diseases and conditions which comprises the removal of the tetrazolyl protecting group in an organic solvent, and in the presence of a Lewis acid. As Lewis acids normally all species are considered which have a vacant orbital and/or an available LUMO and all species with full or partial positive charge. Usually Lewis acids such as boron trifluoride, aluminium trihalide, and/or zinc dihalide are applied.

The preferred embodiment of the present invention provides an improved deprotection reaction leading towards candesartan and pharmaceutically acceptable salts and esters thereof which comprises the removal of the triphenylmethane (trityl) protecting group from the tetrazolyl moiety, in a polar organic solvent, and in the presence of a Lewis acid. As Lewis acid preferably a zinc dihalide is applied, including zinc difluoride, dichloride, dibromide or diiodide. Most preferably zinc dichloride is used.

It has unexpectedly been found that in the preparation of candesartan and its pharmaceutically active esters and salts, preferably candesartan cilexetil, the deprotection reaction of the tetrazolyl protecting group, especially when the tetrazolyl protecting group is trityl, leads to much higher yields if performed in a polar organic solvent, and in the presence of a Lewis acid. The reaction times are shorter when compared to prior art deprotection procedures and consequently, candesartan cilexetil with lower levels of impurities is prepared.

In a further aspect, the present invention provides candesartan cilexetil substantially free of 2-oxo impurities of structural formula (II):

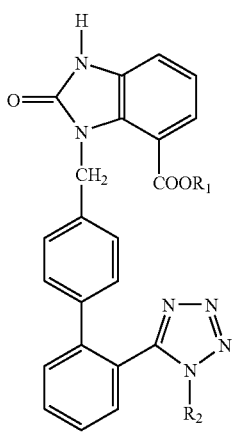

(II)

wherein $R_1$ is alkyl or alkylaryl, such as methyl, ethyl, benzyl etc.; and $R_2$ is H or a tetrazolyl protecting group, such as e.g. the triphenylmethyl (trityl) protection group.

In the following preferred embodiments of the invention are described.

DETAILED DESCRIPTION OF THE INVENTION

The present invention provides an improved synthesis for the manufacture of candesartan cilexetil which comprises the removal of the triphenylmethane (trityl) protecting group in an organic solvent, and in the presence of a Lewis acid.

The starting material, which is a candesartan derivative or its free acid, preferably a candesartan ester, most preferably (+/−)-1-[[(cyclohexyloxy)carbonyl]oxy]ethyl-2-ethoxy-1-[[2'-(N-triphenylmethyltetrazol-5-yl)-1,1'-biphenyl-4-yl] methyl]1H-benzimidazole-7-carboxylate (trityl candesartan cilexetil), may be prepared as described e.g. in *J. Med. Chem.* 1993, 36, 2343-2349, or any other procedure method known in the art, and may be used in its solid or dissolved form. Accordingly, trityl candesartan cilexetil may be used as the isolated compound, in form of a solution or as the unisolated reaction mixture.

The first embodiment of the present invention provides an improved deprotection reaction leading towards candesartan and pharmaceutically acceptable salts and esters thereof which comprises the removal of the protecting group from the tetrazolyl moiety in a polar organic solvent, and in the presence of a Lewis acid, which is a classic electron deficient species, such as e.g. boron trifluoride, aluminium trihalide, zinc dihalide etc. Preferably a zinc dihalide, and most preferably zinc dichloride are applied. In the preferred embodiment, the tetrazolyl protecting group is the triphenylmethyl (trityl) protection group.

A process for the preparation of (+/−)-1-[[(cyclohexyloxy) carbonyl]oxy]ethyl-2-ethoxy-1-[[2'-(1H-tetrazol-5-yl)-1,1'-biphenyl-4-yl]methyl]-1H-benzimidazole-7-carboxylate (candesartan cilexetil) comprises:

i. transesterification or esterification of the tetrazolyl protected candesartan derivative or the tetrazolyl protected candesartan in its acid form into tetrazolyl protected candesartan cilexetil, ii. treating a tetrazolyl protected candesartan cilexetil with a Lewis acid in a suitable organic solvent or in a mixture of suitable organic solvents, iii. adding a second solvent, preferably water, and heating the reaction mixture, iv. isolation of the obtained candesartan cilexetil.

If transesterification of step (i) is carried out on a tetrazolyl protected candesartan derivative, e.g. on ethyl ester of trityl protected candesartan, it is of high importance that after completion of step (i) the content of the tetrazolyl protected candesartan derivative applied, e.g. ethyl ester of trityl protected candesartan is less than 0.5%, as it may otherwise lead to unwished impurities, e.g. ethyl ester of candesartan, which are difficult to remove in step (iv). If esterification of the tetrazolyl protected candesartan in its acid form is being carried out in step (i), attention should be paid to the content of tetrazolyl protected candesartan derivatives, e.g. ethyl ester of trityl protected candesartan. Preferably, the content of tetrazolyl protected candesartan derivatives, e.g. ethyl ester of trityl protected candesartan is less than 0.4%.

In the preferred embodiment the process for the preparation of (+/−)-1-[[(cyclohexyloxy)carbonyl]oxy]ethyl-2-ethoxy-1-[[2'-(1H-tetrazol-5-yl)-1,1'-biphenyl-4-yl]methyl]-1H-benzimidazole-7-carboxylate (candesartan cilexetil) comprises:

ii. treating (+/−)-1-[[(cyclohexyloxy)carbonyl]oxy]ethyl-2-ethoxy-1-[[2'-(N-triphenylmethyltetrazol-5-yl)-1,1'-biphenyl-4-yl]methyl]-1H-benzimidazole-7-carboxylate (trityl candesartan cilexetil) with a Lewis acid in a suitable organic solvent, iii. adding a second solvent, preferably water, and heating the reaction mixture, iv. isolation of the obtained candesartan cilexetil.

A preferred process for the preparation of candesartan cilexetil is that in which the Lewis acid is a zinc dihalide, preferably zinc dichloride. The Lewis acid is added in an amount between 0.4 to 1.5 equivalents, preferably in an amount between 0.6 to 1.2 equivalents, most preferably in an amount between 0.7 to 1.0 equivalents.

The second solvent in step (iii), preferably water, may be added in an amount between 0% (v/v) and 10% (v/v), preferably between 0.5% (v/v) and 10% (v/v), more preferably between 1 and 5%.

As the second solvent a polar solvent may be added, before or during heating. Preferably the second solvent is water.

The reaction mixture in step (iii) is heated at a temperature between 0° C. and 120° C., preferably at reflux temperature, for 0.5 to 10 hours, preferably for 2 to 5 hours.

In the first embodiment alcohols, acetates, ethers, amides, nitrites, halogenated hydrocarbons, ketones, alkanes, cycloalkanes, aromatic hydrocarbons, or organic carbonates are used as suitable organic solvents for the reaction in step (ii). Preferably the organic solvent is an alcohol, and most preferably the organic solvent is methanol.

In the second embodiment mixtures of organic solvents from the first embodiment are used as suitable organic solvents for the reaction in step (ii). Preferably mixtures of an alcohol and an unpolar organic solvent such as e.g. halogenated hydrocarbons, alkanes, cycloalkanes, aromatic hydrocarbons, or organic carbonates are used, more preferably mixtures of an alcohol with a halogenated hydrocarbon are applied and most preferably, the mixtures applied as the reaction solvent in step (ii) are mixtures of methanol and methylene chloride.

The conversion of the starting material is almost complete, as less than 2% of starting material (trityl candesartan cilexetil) remain in the reaction mixture. The amount of the byproduct 2-oxo-candesartan cilexetil in the reaction mixture is less than 2%.

Isolation of the obtained candesartan cilexetil includes crystallization, precipitation, lyophilization, extraction, including exctractions under super-critical conditions or by the use of pressurized gasses, spray-drying or any other procedure known to the person skilled in the art.

In the first embodiment when simple organic solvents are used for the reaction in step (ii), in the isolation step (iv) the reaction mixture is cooled to a temperature below 30° C., neutralized to a pH value between 5 and 8, preferably to a pH value between 6 and 7, with a solution of a base, which may be an inorganic base, such as NaOH, KOH, LiOH, Ca(OH)$_2$, Na$_2$CO$_3$, NaHCO$_3$, K$_2$CO$_3$, KHCO$_3$, inorganic phosphates, or an organic base such as amines. Preferably, carbonates and phosphates are used, and most preferably hydrogencarbonates are applied as bases for the reaction mixture neutralization.

Following the neutralization volatile components of the reaction mixture are evaporated in vacuo, a water immiscible solvent is added to the reaction mixture together with some water and candesartan cilexetil is extracted to the organic phase. Organic fractions are collected, washed with water or brine and dried over a desiccant, e.g. anhydrous sodium or magnesium sulfate (VI). The extractions are performed at a temperature below 50° C., preferably below 30° C., and most preferably below 20° C.

As water immiscible solvents for the extraction acetates (e.g. ethyl acetate, methyl acetate, isopropyl acetate, propyl acetate, butyl acetate, isobutyl acetate), ethers (e.g. diethyl ether, diisopropyl ether, tert-butyl methyl ether), halogenated hydrocarbons (such as methylene chloride), toluene and hydrocarbons (heptane, hexane, cyclohexane) can be used.

The organic phase is partly evaporated in vacuo until between ½ and ⅕ of the starting volume remains in the vessel, and an unpolar solvent is added to the concentrate. As unpolar solvents hydrocarbons (heptane hexane, cyclohexane), toluene and ethers may be added. After the addition of the unpolar solvent, the mixture is stirred and cooled below 20° C. for 2 to 24 h.

In the second embodiment when mixtures of organic solvents are used as suitable organic-solvents for the reaction in step (ii), in the isolation step (iv) the reaction mixture is cooled to a temperature below 30° C., optionally diluted with an unpolar organic solvent (e.g. halogenated hydrocarbons, alkanes, cycloalkanes, aromatic hydrocarbons, organic carbonates) and washed with water or brine. The organic phase is dried over a desiccant, e.g. anhydrous sodium or magnesium sulfate (VI). The extractions are performed at a temperature below 50° C., preferably below 30° C., and most preferably below 20° C. The organic phase is partly or completely evaporated in vacuo, and optionally the residue is diluted with an unpolar organic solvent and then a second organic solvent is added. The preferred first solvent for the dilution of the reaction mixture is methylene chloride and as the second solvent to be added after the evaporation, ethers and esters (such as diethyl ether, ethyl methyl ether, diisopropyl ether tert-butyl methyl ether, methyl cyclopentyl ether, THF, methyl acetate, ethyl acetate, propyl acetate, isopropyl acetate, isobutyl acetate, tert-butyl acetate and butyl acetate), toluene, xylene and cyclohexane may be used. After the addition of the second solvent, the mixture is stirred and cooled below 30° C. for 2 to 24 h.

In the first and in the second embodiment, after the completed isolation step (iv) the precipitated or crystallized product (crude candesartan cilexetil) is collected and dried for up to 10 hours at a temperature between 10° C. and 50° C. until candesartan cilexetil containing less than about 5000 ppm residual solvents is obtained. For the drying of the obtained candesartan cilexetil all drying methods known to the average person skilled in the art may be applied, such as e.g. air drying, vacuum drying, fluid bed drying, including fluid bed drying with humid air or an inert gas, and spray drying. Preferably, vacuum drying is applied.

The crude product may be recrystallized from organic solvents such as alcohols, ketones, esters and nitriles, and/or mixtures thereof. Also, the mixtures of above solvents with ethers, esters, halogenated hydrocarbons and hydrocarbons may be used. The crude product can be also suspended in the organic solvent such as: ethers (diethyl ether, ethyl methyl ether, diisopropyl ether tert-butyl methyl ether, methyl cyclopentyl ether, THF), esters (methyl acetate, ethyl acetate, propyl acetate, isopropyl acetate, isobutyl acetate, tert-butyl acetate and butyl acetate), alkanes (hexane, heptane, petrol ether, cyclohexane), toluene and xylene. The crystalline forms of the products crystallized from above solvents were the same as described in *Chem. Pharm. Bull.* 47 (2) 182-186 (1999).

During the crystallization process and during the filtration solvates of candesartan cilexetil may be formed.

It is important to control size of particles of candesartan cilexetil during its preparation. Average particle size of particles used in our work is 10 to 100 μm, preferably below 50 μm, which are usually obtained by crystallization of candesartan cilexetil from organic solvents or their mixtures with water, while stirring. If unstirred, crystallization from organic solvents or their mixtures with water might also yield bigger particles, e.g. with an average diameter of above 100 μm which need to be milled or processed in any other way which reduces particle size, prior to their application in pharmaceutical formulations. When milling, particles of less then 3 μm average diameter may be produced. For this purpose air jet mills, ball mills or hammer mills are commonly used as milling equipment. However, it is not enough to control only the average size of particles, but also particle size distribution.

Average particle size and particle size distribution is important to assure that the technological process is industriable, i.e. does not cause segregation of ingredients of tabletting mixture if it is not tabletted/compressed just after preparation of tabletting mixture.

Another embodiment of the present invention relates to candesartan cilexetil substantially free of 2-oxo impurities of structural formula (II):

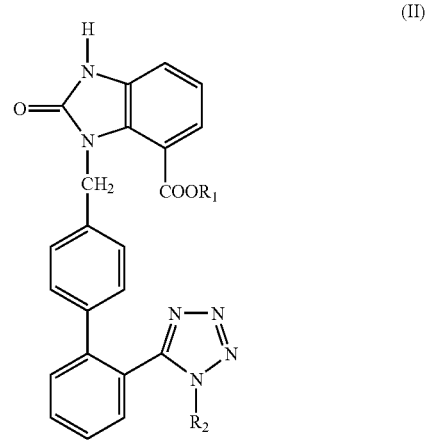

(II)

wherein R$_1$ is: alkyl (especially C$_{1-8}$ alkyl) or alkylaryl (especially C$_{1-6}$ alkyl-C$_{6-10}$ aryl), such as methyl, ethyl, benzyl etc.; and $R_2$ is H or a tetrazolyl protecting group, such as e.g. the triphenylmethyl protection group, and/or substantially free of a tetrazolyl protected or unprotected candesartan derivative, e.g. ethyl ester of trityl protected candesartan or ethyl ester of candesartan of formulas (III) and (IV):

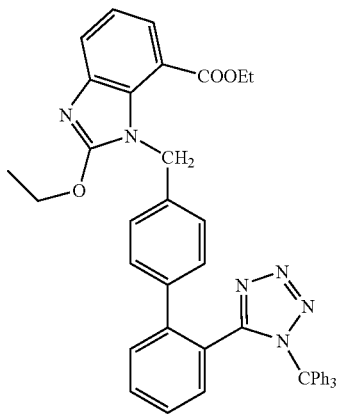

(III)

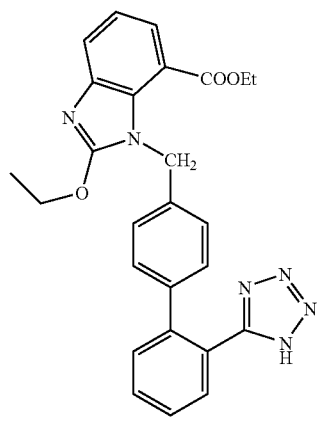

(IV)

Preferably, the present invention provides candesartan cilexetil substantially free of 2-oxo impurities, as well as substantially free of a tetrazolyl protected or unprotected candesartan derivative, e.g. the ethyl ester of trityl protected candesartan or the ethyl ester of candesartan. This invention also provides a method of synthesizing candesartan cilexetil that comprises an amount of 2-oxo impurities not greater than 0.10%, preferably not greater than 0.05%, and an amount of a tetrazolyl protected or unprotected candesartan derivatives, e.g. the ethyl ester of trityl protected candesartan or the ethyl ester of candesartan not greater than 0.15%, preferably not greater than 0.10%. All percentages given herein are by weight.

The 2-oxo impurities and tetrazolyl protected or unprotected candesartan derivatives were determined by means of a HPLC method, comprising:

Equipment
  HPLC: Agilent 1100
  Data evaluation: ChemStation

Chromatographic Conditions:
  Column: Zorbax Eclipse XDB C-18, 1.8 µm, 50×4.6 mm Mobile Phase:
  Solvent A: 0.01M sodium dihydrogenphosphate, pH 2.5
  Solvent B: acetonitrile Gradient:

| Time (min) | % A | % B |
|---|---|---|
| 0 | 55 | 45 |
| 16 | 5 | 95 |
| 18 | 5 | 95 |
| 19 | 55 | 45 |

Post run: 2 min
Column temp.: 30° C.
Flow rate: 1.0 ml/min
Detection: V, 225 nm
Injection: 10 µl Reference Solution (RS)
  RS1: Dissolve 5 mg of candesartan cilexetil standard and 5 mg of each of the candesartan intermediates trityl candesartan cilexetil and trityl candesartan in acetonitrile and dilute to 10.0 ml. RS2: Dilute 1.0 ml of this solution to 100.0 ml with acetonitrile.

Test Solutions (TS)
  TS1: Dilute 20.0 µl of reaction solution to 20.0 ml with acetonitrile.
  TS2: Dissolve about 10 mg of the substance to be examined in acetonitrile and dilute to 25.0 ml with acetonitrile.

When the chromatograms are recorded in the prescribed conditions, the retention time of candesartan is about 7 min, the relative retention time of trityl candesartan cilexetil is about 1.2, the relative retention time of trityl candesartan is about 2.1 and the relative retention times of 2-oxo candesartan cilexetil, $Ph_3COH$, $Ph_3COMe$, $Ph_3COEt$ are about 0.6, 0.8, 1.3, 1.4. The relative retention time of ethyl ester of trityl candesartan is about 1.8 and the relative retention time of ethyl ester of candesartan is about 0.5. The method of evaluation is area %.

The present invention is illustrated by the following Examples without being limited thereto.

Melting points were taken on a Koffler melting point apparatus and IR spectra were taken on a Paragon 100 Perkin-Elmer FT-IR spectrometer.

EXAMPLES

Comparative Example 1

WO 2005/021535, Example 12

A mixture of trityl candesartan cilexetil (0.43 g) and methanol (8.6 ml) was stirred and refluxed for 24 h. After that time the reaction mixture was analyzed by HPLC.
  Candesartan cilexetil: 64.9%
  Trityl candesartan cilexetil: 0.64%
  2-Oxo candesartan cilexetil: 8.0%

The mixture was evaporated to ¼ and after cooling the precipitated crystals were filtered. The filtrate was evaporated and crystallized from cyclohexane. The white crystals were obtained (HPLC Area %: candesartan cilexetil: 76.1%, trityl candesartan cilexetil: 1.2%, 2-oxo candesartan cilexetil: 10.9%

Comparative Example 2

WO2005/037821, Example 5

A solution of trityl candesartan cilexetil (0.43 g), formic acid (0.38 ml), methylene chloride (1.7 ml) and methanol (0.9 ml) was stirred at 25° C. for 5 h. The reaction mixture was analyzed after that time:

HPLC area %, 5 h: candesartan cilexetil: 68.1%, trityl candesartan cilexetil: 12.4%, 2-oxo candesartan cilexetil: 0.5%

HPLC area %, 7 h: candesartan cilexetil: 64.6%, trityl candesartan cilexetil: 14.9%, 2-oxo candesartan cilexetil: 1.7%

HPLC area %, 23 h: candesartan cilexetil: 61.6%, trityl candesartan cilexetil: 18.4%, 2-oxo candesartan cilexetil: 2.2%.

Example 1

The mixture of 0.43 g (0.5 mmol) of trityl candesartan cilexetil, 15 ml of methanol, 0.05 g (0.37 mmol) of $ZnCl_2$ and 0.4 ml of water is stirred under reflux temperature for 2.5 h. The reaction mixture is analyzed (Area % HPLC: candesartan cilexetil: 75.5%, trityl candesartan cilexetil: 1.2%, 2-oxo candesartan cilexetil: 1.6%) and cooled to room temperature. Then, the mixture is neutralized to pH 6.11 by addition of a saturated solution of $NaHCO_3$ and methanol is evaporated. Ethyl acetate (15 ml) and water (10 ml) are added and the mixture is stirred. After the separation of phases, the organic phase is washed with 10 ml of water. The organic phase is dried over $Na_2SO_4$, filtered and evaporated to ¼ of the starting volume. To the oily remainder, 10 ml of heptane are added and cooled below 0° C. The precipitated product is collected by filtration and dried.

Example 2

A mixture of 1.55 g (1.8 mmol) of trityl candesartan cilexetil, 5.4 ml of methanol, 22 ml of methylene chloride, 0.05 g (1.61 mmol) of $ZnCl_2$ and 0.5 ml of water is stirred under reflux temperature for 5 h. The reaction mixture is analyzed (Area % HPLC: candesartan cilexetil: 76.3%, trityl candesartan cilexetil: 1.8%, 2-oxo candesartan cilexetil: 0.7%, ethyl ester of candesartan 0.09%.) and cooled to room temperature. Then, to the mixture 36 ml of methylene chloride and 55 ml of water is added. The phases were separated and organic phase is washed with 2×55 ml of water. Organic phase is dried over $Na_2SO_4$, filtered and evaporated to the oily residue. This residue is dissolved in 1.6 ml of methylene chloride and then 16 ml of isopropyl acetate is added. The mixture is stirred at 0° C. for 24 h. The precipitated product is collected by filtration and dried. After that the product was suspended in 5 ml of tert-butyl methyl ether. The mixture is stirred for 2 h. The product is collected by filtration and dried at 40° C. for 2 h in vacuum drier (0.7 g). Area % HPLC: Candesartan cilexetil: 99.6%, 2-oxo candesartan cilexetil: 0.00%, ethyl ester of candesartan 0.08%.

What is claimed is:

1. A process for the preparation of candesartan cilexetil of formula (I)

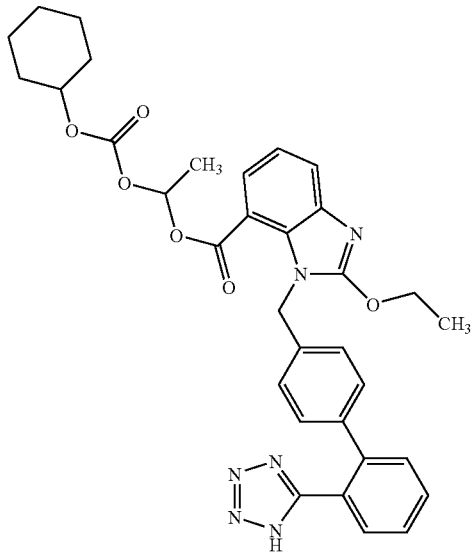

which comprises deprotection of the triphenylmethane (trityl) of (+/−)-1-[[cyclohexyloxy) carbonyl]oxy]-ethyl-2-ethoxy-1-[[2'-(N-triphenyl-methyltetrazol-5-yl)-1,1'-biphenyl-4-yl]methyl]-1H-benzimidazole-7-carboxylate (trityl candesartan cilexetil) in an organic solvent and in the presence of a Lewis acid selected from the group consisting of boron trifluoride, aluminum trihalide and zinc dihalide, adding a second solvent and heating the reaction mixture, isolation of the obtained candesartan cilexetil of formula (I).

2. A process according to claim 1, characterized in that the triphenylmethane (trityl) is the triphenylmethyl (trityl) protecting group.

3. A process according to claim 1, characterized in that the organic solvent is a solvent or a solvent mixture selected from the group of alcohols, acetates, ethers, amides, nitriles, halogenated hydrocarbons, ketones, alkanes, cycloalkanes, aromatic hydrocarbons and organic carbonates.

4. A process according to claim 3, characterized in that the solvent mixture consists of a polar solvent and an unpolar solvent.

5. A process according to claim 4, characterized in that the polar solvent is chosen from the group of alcohols, amides, ketones and nitriles.

6. A process according to claim 4, characterized in that the unpolar solvent is selected from the group consisting of halogenated hydrocarbons, alkanes, cycloalkanes, aromatic hydrocarbons and organic carbonates.

7. A process according to claim 4, characterized in that the polar organic solvent is methanol.

8. A process according to claim 4, characterized in that the unpolar organic solvent is methylene chloride.

9. A process according to claim 4, characterized in that the reaction is carried out at a temperature between 20° C. to 100° C.

10. A process according to claim 1, characterized in that the Lewis acid is zinc dichloride.

11. A process according to claim 1, characterized in that the Lewis acid is boron trifluoride.

12. A process according to any of claims 1, 10 and 11, characterized in that the Lewis acid is added in an amount between 0.4 to 1.5 equivalents, preferably in an amount between 0.6 to 1.2 equivalents, most preferably in an amount between 0.7 to 1.0 equivalents.

13. A process for the preparation of candesartan cilexetil which comprises:
   i. transesterification or esterification of the trityl candesartan cilexetil or the trityl candesartan cilexetil in its acid form into trityl candesartan cilexetil,
   ii. treating a trityl candesartan cilexetil with a Lewis acid selected from the group consisting of boron trifluoride, aluminium trihalide and zinc dihalide in a organic solvent or in a mixture of organic solvents,
   iii. adding a second solvent, preferably water, and heating the reaction mixture,
   iv. isolation of the obtained candesartan cilexetil.

14. A process for the preparation of candesartan cilexetil which comprises:
   ii. treating (+/−)-1-[[(cyclohexyloxy)carbonyl]oxy]-ethyl-2-ethoxy-1-[[2'-(N-triphenylmethyltetrazol-5-yl)-1,1'-biphenyl-4-yl]methyl]-1H-benzimidazole-7-carboxylate (trityl candesartan cilexetil) with a Lewis acid selected from the group consisting of boron trifluoride, aluminium trihalide and zinc dihalide in a organic solvent or in the mixture of the organic solvents,
   iii. Adding a second solvent, preferably water, and heating the reaction mixture, and
   iv. isolation of the obtained candesartan cilexetil.

15. A process in according to any of claims 13 and 14, characterized in that the second solvent of step (iii), preferably water, is added in an amount between 0 (v/v) and 10% (v/v), preferably between 1 and 5%.

16. A process according to any of claims 13 and 14, characterized in that the reaction mixture is heated at a temperature between 0° C. and 120° C., preferably at reflux temperature, for 0.5 hours to 10 hours, preferably for 2 to 5 hours.

17. A process according to any of claims 1, 13 and 14, characterized in that alcohols, acetates, ethers, amides, nitriles and mixtures thereof are used as organic reaction solvents.

18. A process according to claim 17, characterized in that methanol is used as the reaction solvent in step (ii).

19. A process according to any of claims 1, 13 and 14, characterized in that isolation of the obtained candesartan cilexetil includes crystallization, precipitation, lyophilization, extraction, including extractions under super-critical conditions or by the use of pressurized gasses, spray-drying or any other procedure known to the person skilled in the art.

20. A process according to claims 1, 13 and 14, characterized in that candesartan cilexetil containing less than 5000 ppm residual solvents is obtained.

* * * * *

UNITED STATES PATENT AND TRADEMARK OFFICE
CERTIFICATE OF CORRECTION

PATENT NO.         : 7,884,212 B2  
APPLICATION NO.    : 12/089444  
DATED              : February 8, 2011  
INVENTOR(S)        : Silvo Zupancic Page 1 of 1

It is certified that error appears in the above-identified patent and that said Letters Patent is hereby corrected as shown below:

In the Claims:

Column 10, Claim 1, line 2, insert the opening -- ( -- before the word "cyclohexyloxy)" to read "[[(cyclohexyloxy)".

Column 10, Claim 1, line 3, insert the -- ' -- after "N" to read "N'".

Column 10, Claim 1, line 8, change "isolation of" to read "isolating".

Column 10, Claim 2, lines 35-37, cancel Claim 2 [A process according to Claim 1, characterized in that the triphenylmethane (trityl) is the triphenylmethyl (trityl) protecting group.].

Column 11, Claim 14, line 8, change "a organic" to read "an organic".

Column 12, Claim 15, line 3, insert -- % -- after "0" to read "0%".

Signed and Sealed this  
Twelfth Day of July, 2011

David J. Kappos  
*Director of the United States Patent and Trademark Office*

UNITED STATES PATENT AND TRADEMARK OFFICE
CERTIFICATE OF CORRECTION

PATENT NO.        : 7,884,212 B2                                       Page 1 of 2
APPLICATION NO.   : 12/089444
DATED             : February 8, 2011
INVENTOR(S)       : Silvo Zupancic It is certified that error appears in the above-identified patent and that said Letters Patent is hereby corrected as shown below:

Delete the title page and substitute therefore the attached title page showing the corrected number of claims in patent.

In the Claims:
Column 10, line 27, Claim 1, insert the opening -- ( -- before the word "cyclohexyloxy)" to read "[[(cyclohexyloxy)".
Column 10, line 28, Claim 1, insert the -- ' -- after "N" to read "N'".
Column 10, lines 33-34, Claim 1, change "isolation of" to read "isolating".
Column 10, lines 35-37, Claim 2, cancel Claim 2 [A process according to Claim 1, characterized in that the triphenylmethane (trityl) is the triphenylmethyl (trityl) protecting group.].
Column 11, line 22 (Claim 14, line 8) change "a organic" to read "an organic".
Column 12, line 3, Claim 15, insert -- % -- after "0" to read "0%".

This certificate supersedes the Certificate of Correction issued July 12, 2011.

Signed and Sealed this
Sixteenth Day of August, 2011

David J. Kappos
*Director of the United States Patent and Trademark Office*

CERTIFICATE OF CORRECTION (continued)

(12) United States Patent
Zupancic

(10) Patent No.: US 7,884,212 B2
(45) Date of Patent: Feb. 8, 2011

(54) PROCESS FOR THE PREPARATION OF CANDESARTAN CILEXETIL

(76) Inventor: Silvo Zupancic, Zupnca 4b 8000, Novo mesto (SI)

(*) Notice: Subject to any disclaimer, the term of this patent is extended or adjusted under 35 U.S.C. 154(b) by 95 days.

(21) Appl. No.: 12/089,444

(22) PCT Filed: Sep. 29, 2006

(86) PCT No.: PCT/EP2006/009489

§ 371 (c)(1),
(2), (4) Date: Sep. 8, 2008

(87) PCT Pub. No.: WO2007/042161

PCT Pub. Date: Apr. 19, 2007

(65) Prior Publication Data

US 2009/0318706 A1  Dec. 24, 2009

(30) Foreign Application Priority Data

Oct. 7, 2005 (SI) .............................. 200500283
Mar. 3, 2006 (SI) .............................. 200600041

(51) Int. Cl.
*C07D 233/00* (2006.01)
*C07D 249/08* (2006.01)
(52) U.S. Cl. .................................. 548/250; 548/300.1
(58) Field of Classification Search ........... 548/250, 548/300.1

See application file for complete search history.

(56) References Cited

U.S. PATENT DOCUMENTS 5,578,733 A * 11/1996 Shida et al. ................ 548/253

FOREIGN PATENT DOCUMENTS

| EP | 0 459 136 A1 | 12/1991 |
| EP | 0 668 272 A2 | 8/1995 |
| EP | 0 720 982 A1 | 10/1996 |
| WO | 2005/037821 A2 | 4/2005 |
| WO | 2005/051928 A1 | 6/2005 |
| WO | 2005/021535 A2 | 10/2005 |
| WO | WO A 2007/074399 | 7/2007 |

OTHER PUBLICATIONS

Lu R J et al: "Detritylation with ytterbium triflate" Tetrahedron Letters, Elsevier, Amsterdam, NL, vol. 41, No. 16, Apr. 2000, pp. 2817-2819, XP004195678 ISSN: 0040-4039, p. 2817, paragraphs 1,4.
Römpp Lexikon: Lewis Säure [Online] 2006, Georg Thieme Verlag, XP002407601 Retrieved from Internet: URL: http://roempp.com> [retrieved on Nov. 15, 2006].
U.S. Appl. No. 60/687,305, Nuria Soldevilla Madrid.
U.S. Appl. No. 11/921,677, filed Jun. 6, 2006, Nuria Soldevilla Madrid.

* cited by examiner

*Primary Examiner* — Susannah Chung
(74) *Attorney, Agent, or Firm* — LaRiviere, Grubman & Payne, LLP

(57) ABSTRACT

The present invention provides an improved synthesis for the manufacture of candesartan and pharmaceutically acceptable salts and esters thereof as active ingredients of a medicament for the treatment of hypertension and related diseases and conditions which comprises the removal of the tetrazolyl protecting group in an organic solvent, and in the presence of a Lewis acid.

19 Claims, No Drawings